(12) United States Patent
Lai et al.

(10) Patent No.: US 10,613,167 B2
(45) Date of Patent: Apr. 7, 2020

(54) MAGNETIC RESONANCE IMAGING METHOD AND SYSTEM

(71) Applicant: General Electric Company, Schenectady, NY (US)

(72) Inventors: Yongchuan Lai, Beijing (CN); Weiwei Zhang, Brookfield, WI (US); Tongzhou Wang, Beijing (CN); Hongbin Wang, Beijing (CN); Yoshihiro Tomoda, Hino (JP); Mitsuhiro Bekku, Hino (JP); Shaorong Chang, Hartland, WI (US); Graeme Colin McKinnon, Hartland, WI (US)

(73) Assignee: General Electric Company, Schenectady, NY (US)

( * ) Notice: Subject to any disclaimer, the term of this patent is extended or adjusted under 35 U.S.C. 154(b) by 225 days.

(21) Appl. No.: 15/692,101

(22) Filed: Aug. 31, 2017

(65) Prior Publication Data

US 2018/0059195 A1   Mar. 1, 2018

(30) Foreign Application Priority Data

Aug. 31, 2016 (CN) .......................... 2016 1 0786981

(51) Int. Cl.
*G01R 33/381* (2006.01)
*G01R 33/565* (2006.01)
*A61N 1/40* (2006.01)
*A61N 2/02* (2006.01)
*G01R 33/38* (2006.01)
*G01R 33/385* (2006.01)
*G01R 33/421* (2006.01)
*G01R 33/44* (2006.01)

(52) U.S. Cl.
CPC .......... *G01R 33/381* (2013.01); *A61N 1/403* (2013.01); *A61N 2/02* (2013.01); *G01R 33/3802* (2013.01); *G01R 33/385* (2013.01); *G01R 33/421* (2013.01); *G01R 33/445* (2013.01); *G01R 33/565* (2013.01)

(58) Field of Classification Search
CPC .............. G01R 33/381; G01R 33/565; G01R 33/3802; G01R 33/385; G01R 33/421; G01R 33/445; A61N 1/403; A61N 2/02
See application file for complete search history.

(56) References Cited

U.S. PATENT DOCUMENTS

| 7,288,937 B2 * | 10/2007 | Nabetani | G01R 33/3415 324/307 |
|---|---|---|---|
| 2005/0237056 A1 * | 10/2005 | Nabetani | G01R 33/3415 324/302 |
| 2017/0115369 A1 * | 4/2017 | De Weerdt | G01R 33/4824 |

* cited by examiner

Primary Examiner — Dixomara Vargas

(57) ABSTRACT

The present invention provides a magnetic resonance imaging method and system, the method comprising performing the following steps at least once: a composition step: performing image composition processing on raw images received by a receiving coil that is pre-determined as an artifact coil and a receiving coil that is pre-determined as a non-artifact coil to obtain a composite image; and a correction step: obtaining a product of the above composite image and space sensitivity of the above artifact coil to replace the raw image received by the above artifact coil, and performing the above composition step again.

16 Claims, 4 Drawing Sheets

MAGNETIC RESONANCE IMAGING METHOD AND SYSTEM

CROSS-REFERENCE TO RELATED APPLICATION

This application claims priority to Chinese Patent Application No. 201610786981.6, filed on Aug. 31, 2016, the entirety of which is incorporated herein by reference.

BACKGROUND

Embodiments of the subject matter disclosed herein relate to medical imaging, and more particularly, to a magnetic resonance imaging method and system.

Multi-channel parallel imaging technology has been applied in magnetic resonance imaging, which has advantages such as high signal-to-noise ratio, high resolution, fast imaging, and the like. In order to improve problems in image quality that results from uneven received signals, the multi-channel parallel imaging technology utilizes an image composition processing method (e.g., an image processing method of sum of squares) to composite uneven images obtained from coil channels at different positions resulting in a relatively even image. Although such image processing method can improve the image quality, there still exists relatively obvious artifacts in obtained images.

SUMMARY

One objective of the present invention is to provide a novel magnetic resonance imaging method and magnetic resonance imaging system such that an artifact in a magnetic resonance image can be effectively eliminated.

An exemplary embodiment provides a magnetic resonance imaging method, comprising performing the following steps: a composition step of performing image composition processing on raw images received by a receiving coil that is pre-determined as an artifact coil and a receiving coil that is pre-determined as a non-artifact coil to obtain a composite image; and a correction step of obtaining a product of the above composite image and space sensitivity of the above artifact coil to replace the raw image received by the above artifact coil, and performing the above composition step again.

An exemplary embodiment provides a magnetic resonance imaging system, comprising a composition module and a correction module. The composition module is used for performing image composition processing on raw images received by a receiving coil that is pre-determined as an artifact coil and a receiving coil that is pre-determined as a non-artifact coil to obtain a composite image. The correction module is used for obtaining a product of the above composite image and space sensitivity of the above artifact coil to replace the raw image received by the above artifact coil, and making the above composition module perform the image composition processing again in order to obtain a new composite image.

Various other features and advantages will be made apparent from the following detailed description and the drawings.

BRIEF DESCRIPTION OF THE DRAWINGS

Embodiments of the subject matter disclosed herein can be understood better in light of the description of exemplary embodiments with reference to the accompanying drawings.

DETAILED DESCRIPTION

Hereafter, a detailed description will be given for preferred embodiments of the present disclosure. It should be pointed out that in the detailed description of the embodiments, for simplicity and conciseness, it is impossible for the description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art associated with the contents disclosed in the present disclosure, which should not be regarded as insufficient disclosure of the present disclosure.

Unless defined otherwise, all the technical or scientific terms used in the claims and the detailed description should have the same meanings as commonly understood by one of ordinary skilled in the art to which the present disclosure belongs. The terms "first", "second" and the like in the detailed description and the claims of the present disclosure do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
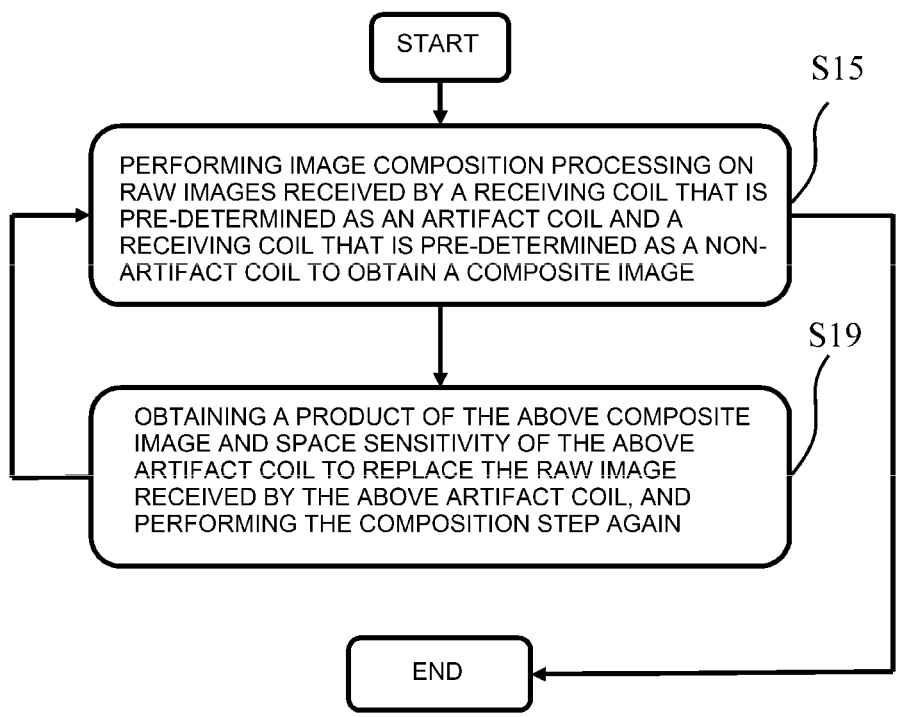
FIG. 1 is a flow chart of a magnetic resonance imaging method provided by an embodiment.

FIG. 1 is a flow chart of a magnetic resonance imaging method provided by an embodiment. As shown in FIG. 1, the method includes performing the following composition step S15 and correction step S19 at least once.

The composition step S15 of performing image composition processing on raw images received by a receiving coil that is pre-determined as an artifact coil and a receiving coil that is pre-determined as a non-artifact coil to obtain a composite image.

The correction step S19 of multiplying the above composite image by space sensitivity of the artifact coil to replace the raw image received by the artifact coil, and performing the composition step S15 again.

The above artifact coil may be, for example, a receiving coil that is nearer to an artifact source, and the non-artifact coil may be a receiving coil that is farther from the artifact source. The artifact source may be understood as a position at which an artifact is generated in a magnetic resonance imaging system. In an embodiment, the position may be determined by analyzing a magnetic resonance image, and may also be determined by emulating a gradient coil system in the magnetic resonance imaging system.

Optionally, the above composition step S15 may include extracting a root from a sum of squares of amplitudes of the raw image received by the artifact coil and the raw image received by the non-artifact coil to obtain the composite image. For example, the composite image may be obtained by the following Equation (1):

$$I_C = \sqrt{\text{abs}(I_{b1})^2 + \text{abs}(I_{b2})^2 \ldots + \text{abs}(I_{g1})^2 + \text{abs}(I_{g2})^2 \ldots} \quad (1)$$

In the above Equation (1), $I_C$ is a composite image, $I_{b1}$, $I_{b2}$, . . . are raw images received by artifact coils respectively, and the number of the artifact coils may be one or more than one. $I_{g1}$, $I_{g2}$, . . . are raw images received by non-artifact coils respectively, and the number of the non-artifact coils may also be one or more than one.

Optionally, the above composition step S15 may include extracting a root from a sum of a product of the raw image received by the artifact coil and its conjugated image and a product of the raw image received by the non-artifact coil and its conjugated image to obtain the composite image. For example, the composite image may be obtained by the following Equation (2):

$$I_C = I_{b1} \times C_{b1}' + I_{b2} \times C_{b2}' \ldots + I_{g1} \times C_{g1}' + I_{g2} \times C_{g2}' \quad (2)$$

In the Equation (2), $C_{b1}'$ and $C_{b2}'$ are conjugated images of space sensitivity received by the artifact coils respectively, and $C_{g1}'$ and $C_{g2}'$ are conjugated images of space sensitivity received by the non-artifact coils respectively.

After the composite image $I_C$ has been obtained in the above way, in the step S19, the composite image $I_C$ may be multiplied by the space sensitivity $C_{bi}$ of the artifact coil so as to obtain corrected images $I_{bc1}$, $I_{bc2}$, . . . of the artifact coils to replace the above raw images $I_{b1}$, $I_{b2}$, . . . received by the artifact coils respectively, and a new composite image is obtained by the following Equations (3) or (4). The steps are iterated so until the artifact of the composite image is reduced to some extent.

For example, the Equation (3) and the Equation (4) may be:

$$I_C = \sqrt{\text{abs}(I_{bc1})^2 + \text{abs}(I_{bc2})^2 \ldots + \text{abs}(I_{g1})^2 + \text{abs}(I_{g2})^2 \ldots} \quad (3)$$

$$I_C = I_{bc1} \times C_{b1}' + I_{bc2} \times C_{b2}' \ldots + I_{g1} \times C_{g1}' + I_{g2} \times C_{g2}' \ldots \quad (4)$$

The space sensitivity of the receiving coil may be obtained by many methods, which is common technology in the art and will not be repeatedly described in details herein.

In the step S19, "multiplying the composite image by the space sensitivity of the artifact coil" may include multiplying a module of the composite image by the space sensitivity of the artifact coil and phase distribution information of the raw image received by the artifact coil.

Figure 2:
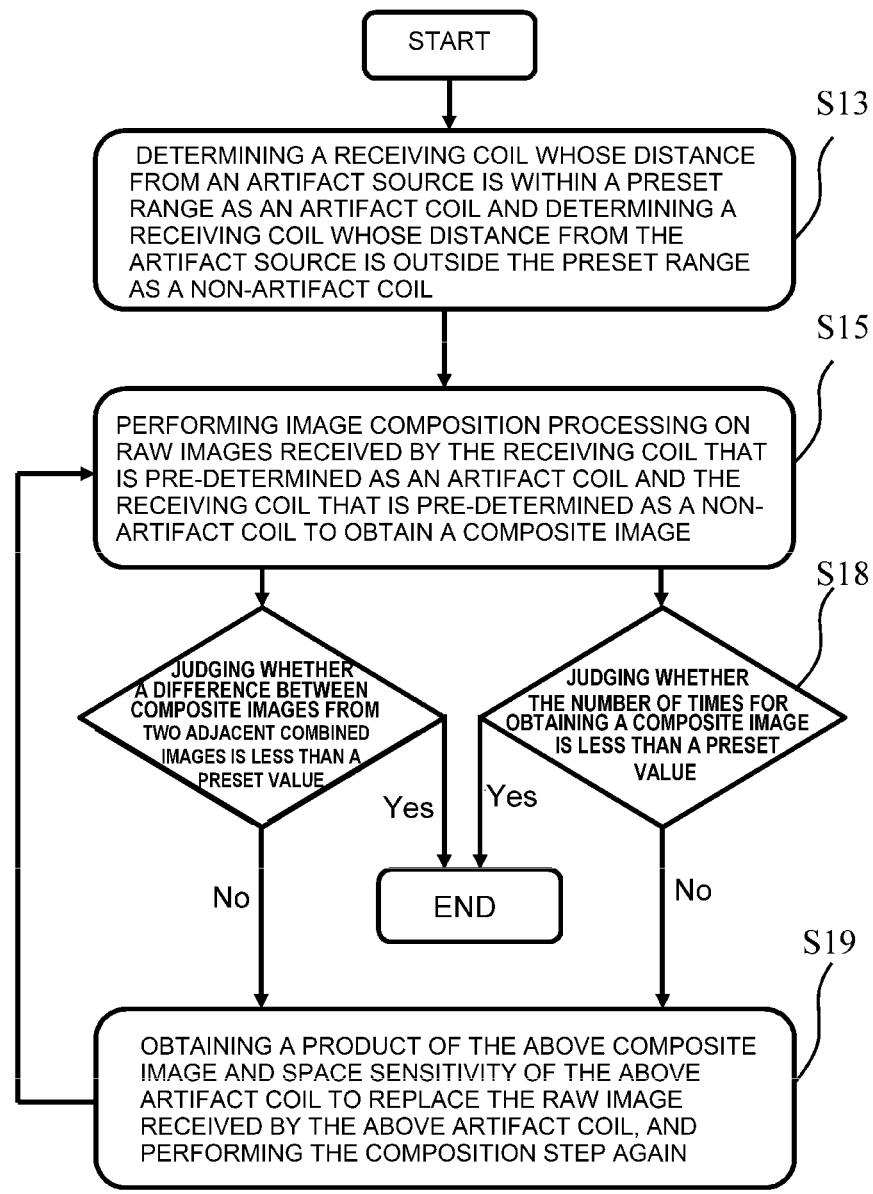
FIG. 2 is a flow chart of a magnetic resonance imaging method provided by another embodiment.

FIG. 2 is a flow chart of a magnetic resonance imaging method provided by one embodiment of the present invention. As shown in FIG. 2, whether an iteration of the composition step S15 and the correction step S19 has been completed may be further determined by a difference between composite images from two adjacent combined images, and iteration times may also be preset according to experience to allow the eventually obtained composite image to meet a quality requirement. For example, a first judgment step S16 or a second judgment step S18 may also be included between the composition step S15 and the correction step S19.

The first judgment step S16 of judging whether a difference between composite images from two adjacent combined images is less than a preset value; if it is, ending the steps; if it is not, performing the above correction step S19 and composition step S15 again.

The second judgment step S18 of judging whether the number of times for performing the composition step S15 has reached a preset value; if it has, ending the steps; if it has not, performing the correction step S19 and the composition step S15 again.

Optionally, before the composition step S15, a coil determining step S13 may further be included: determining a receiving coil whose distance from the artifact source is within a preset range as an artifact coil, and determining a receiving coil whose distance from the artifact source is outside the preset range as a non-artifact coil.

Optionally, before the coil determining step S13, the following steps may further be included. Determining a three-dimensional (3D) position coordinate on which an artifact is generated in the magnetic resonance imaging system by analyzing the magnetic resonance image, and determining a position of the artifact source according to the 3D position coordinate; or emulating a gradient coil system in the magnetic resonance imaging system, determining the 3D position coordinate on which the artifact is generated according to the emulating result, and determining the position of the artifact source according to the 3D position coordinate.

For example, after the gradient coil system has been emulated, a position at which an obvious attenuation appears in the emulating curve may be determined as an artifact source.

Figure 3:
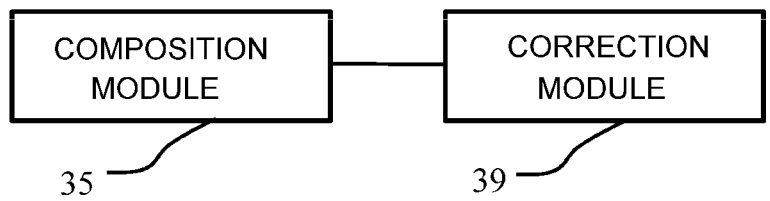
FIG. 3 is a block diagram of a magnetic resonance imaging system provided by an embodiment.

FIG. 3 is a block diagram of a magnetic resonance imaging system provided by one embodiment of the present invention. As shown in FIG. 3, the system may include a composition module 35 and a correction module 39. The composition module 35 is used for performing image composition processing on raw images received by a receiving coil that is pre-determined as an artifact coil and a receiving coil that is pre-determined as a non-artifact coil to obtain a composite image. The correction module 39 is used for multiplying the above composite image by space sensitivity of the artifact coil to replace the raw image received by the artifact coil and sending it to the above composition module 35, to make the above composition module to perform the image composition processing again and obtain a new composite image.

Optionally, the above composition module 35 may be used for extracting a root from a sum of squares of amplitudes of the raw image received by the artifact coil and the raw image received by the non-artifact coil to obtain the composite image. For example, the composite image may be obtained by the above Equation (1).

Optionally, the above composition module 35 may further be used for extracting a root from a sum of a conjugate product of the raw image received by the artifact coil and space sensitivity of its coil and a conjugate product of the raw image received by the non-artifact coil and space sensitivity of its coil to obtain the composite image. For example, the composite image may be obtained by the above Equation (2).

Optionally, the above correction module 39 may be used for multiplying a module of the composite image by the space sensitivity of the artifact coil and phase distribution information of the raw image received by the artifact coil to replace the raw image received by the artifact coil.

Figure 4:
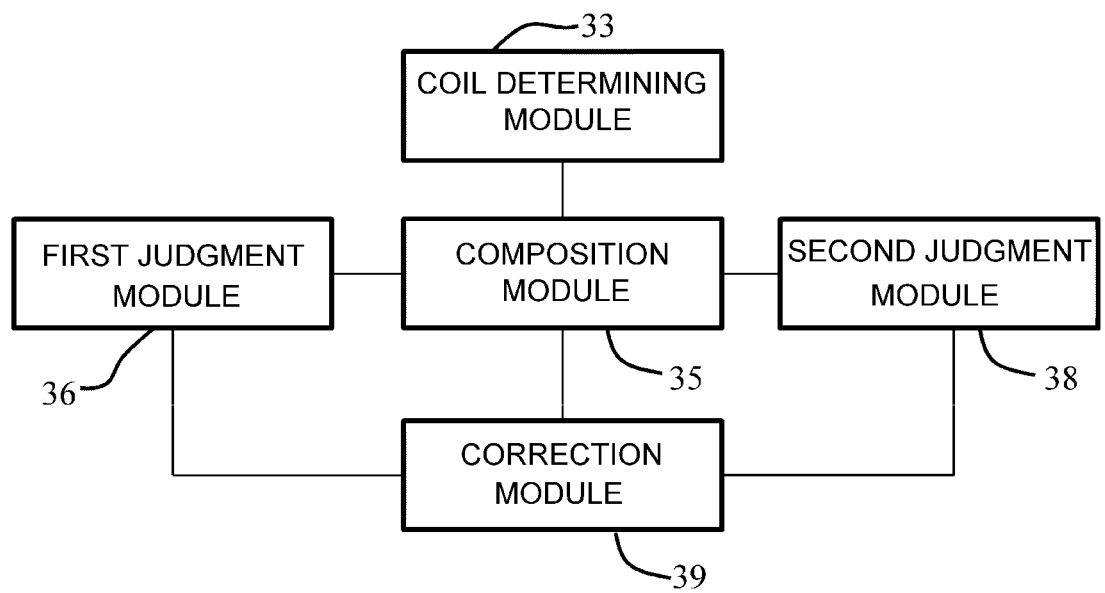
FIG. 4 is a block diagram of a magnetic resonance imaging system provided by another embodiment.

FIG. 4 is a block diagram of a magnetic resonance imaging system provided by another embodiment of the present invention. As shown in FIG. 4, the magnetic resonance imaging system according to the embodiment of the present invention may further include a first judgment module 36, which is used for judging whether a difference between composite images from two adjacent combined images by the composition module 35 is less than a preset value; if it is, controlling the correction module 39 and the composition module 35 to stop operating; if it is not, controlling the correction module 39 and the composition module 35 to operate again.

Optionally, the magnetic resonance imaging system according to the embodiment of the present invention may further include a second judgment module 38, which is used for judging whether the number of times for obtaining a composite image by the composition module 35 has reached a preset value; if it has, controlling the correction module 39 and the composition module 35 to stop operating; if it has not, controlling the correction module 39 and the composition module 35 to operate again.

Optionally, the magnetic resonance imaging system according to the embodiment of the present invention may further include a coil determining module 33, which is used for determining a receiving coil whose distance from the artifact source is within a preset range as an artifact coil and determining a receiving coil whose distance from the artifact source is outside the preset range as a non-artifact coil.

Optionally, the magnetic resonance imaging system according to the embodiment of the present invention may further include a first artifact source determining module, which is used for analyzing a magnetic resonance image to determine a 3D position coordinate on which an artifact is generated in the magnetic resonance imaging system, and determining the position of the artifact source according to the 3D position coordinate.

Or, the magnetic resonance imaging system according to the embodiment of the present invention may further include a second artifact source determining module. The above second artifact source determining module may be used for emulating a gradient coil system in the magnetic resonance imaging system, determining the 3D position coordinate on which an artifact is generated according to the emulating result, and determining the position of the artifact source according to the 3D position coordinate.

The magnetic resonance imaging method and system according to the embodiments of the present invention multiply a composite image of multi-channel images by space sensitivity of a multi-channel coil and correspondingly replace an image of a channel pre-determined as an artifact coil with the image obtained by the above multiplying. In this way, the image of the artifact coil has been corrected, while the image of the non-artifact coil can be retained, and a composite image with less artifact is obtained eventually by iteration, thereby improving image quality.

Figure 5:
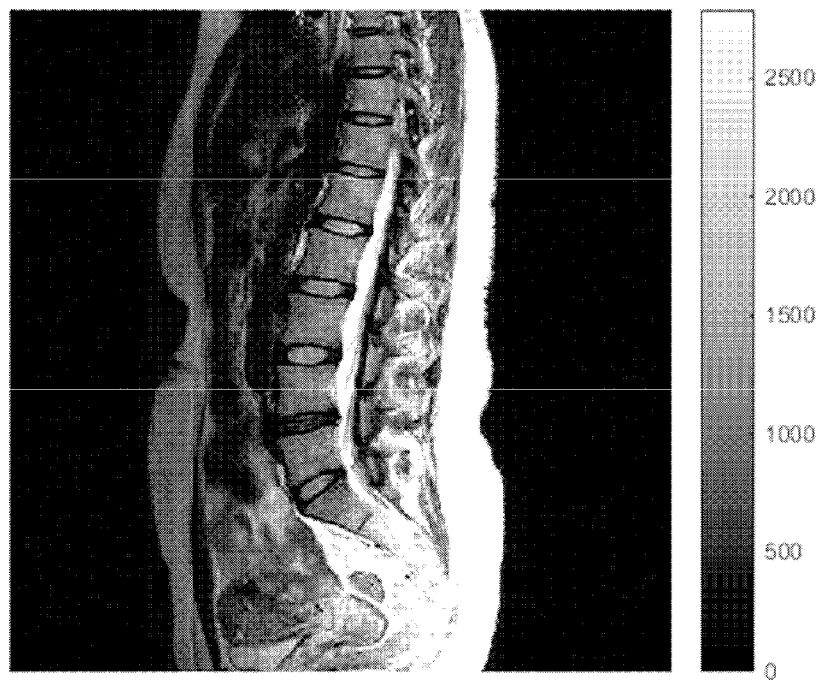
FIG. 5 is a tissue image obtained by an existing magnetic resonance imaging method.
Figure 6:
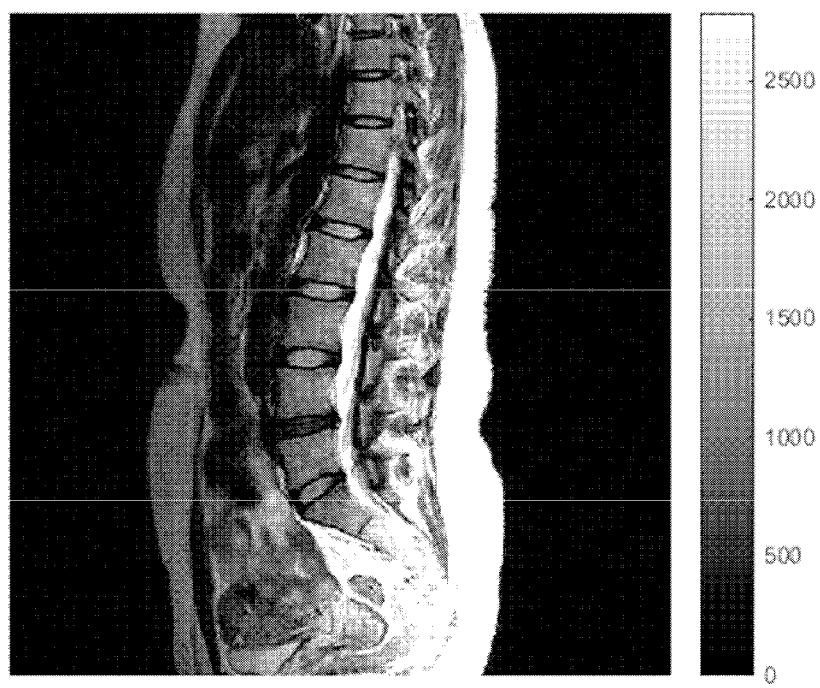
FIG. 6 is a tissue image obtained by a magnetic resonance imaging method according to an embodiment.

FIG. 5 is a tissue image obtained by the existing magnetic resonance imaging method; and FIG. 6 is a tissue image obtained by a magnetic resonance imaging method according to embodiments of the present invention. As can be seen from comparison, compared with FIG. 5, the artifact in the tissue image of FIG. 6 has been reduced obviously.

This written description uses examples to disclose the subject matter of this disclosure, including the best mode, and to enable any person skilled in the art to practice the subject matter, including making and using any apparatus, devices or systems, and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A magnetic resonance imaging method performed by a magnetic resonance imaging system, the method comprising:
   a composition step of performing, by a composition module, image composition processing on raw images received by a receiving coil that is pre-determined as an artifact coil and a receiving coil that is pre-determined as a non-artifact coil to obtain a composite image;
   a correction step of obtaining, by a correction module, a product of the composite image and space sensitivity of the artifact coil to replace the raw image received by the artifact coil; and
   a first judgment step of determining, by a first judgment module, whether a difference between two adjacent composite images is less than a preset value; if it is, stopping operating; if it is not, performing the composition step and the correction step again.

2. The magnetic resonance imaging method according to claim 1, wherein the composition step comprises extracting, by the composition module, a root from a sum of squares of amplitudes of a raw image received by the artifact coil and a raw image received by the non-artifact coil to obtain the composite image.

3. The magnetic resonance imaging method according to claim 1, wherein the composition step comprises extracting, by the composition module, a root from a sum of a conjugate product of the raw image received by the artifact coil and space sensitivity of its coil and a conjugate product of the raw image received by the non-artifact coil and space sensitivity of its coil to obtain the composite image.

4. The magnetic resonance imaging method according to claim 1, further comprising a coil determining step of determining, by a coil determining module, a receiving coil whose distance from an artifact source is within a preset range as an artifact coil and determining a receiving coil whose distance from the artifact source is outside of the preset range as a non-artifact coil.

5. The magnetic resonance imaging method according to claim 4, further comprising determining, by a first artifact source determining module, a three-dimensional (3D) position coordinate on which an artifact is generated in a magnetic resonance imaging system by analyzing a magnetic resonance image, and determining a position of the artifact source according to the 3D position coordinate.

6. The magnetic resonance imaging method according to claim 5, further comprising emulating, by a second artifact source determining module, a gradient coil in the magnetic resonance imaging system, determining a 3D position coordinate on which an artifact is generated according to an emulating result, and determining a position of the artifact source according to the 3D position coordinate.

7. The magnetic resonance imaging method according to claim 1, wherein the correction step of obtaining a product of the composite image and space sensitivity of the artifact coil comprises multiplying, by the correction module, a module of the composite image by the space sensitivity of the artifact coil and phase distribution information of the raw image received by the artifact coil.

8. The magnetic resonance imaging method according to claim 1, further comprising determining, by a second judgment module, whether the number of times for performing the composition step has reached a preset value; if it has, ending the steps; and if it has not, performing the correction step and the composition step again.

9. A magnetic resonance imaging system, comprising:
a composition module for performing image composition processing on raw images received by a receiving coil that is pre-determined as an artifact coil and a receiving coil that is pre-determined as a non-artifact coil to obtain a composite image;
a correction module for obtaining a product of the composite image and space sensitivity of the artifact coil to replace the raw image received by the artifact coil; and
a first judgment module for determining whether a difference between two adjacent composite images is less than a preset value; if it is, controlling the composition module and the correction module to stop operating; if it is not, controlling the composite module and the correction module to operate again.

10. The magnetic resonance imaging system according to claim 9, wherein the composition module is used for extracting a root from a sum of squares of amplitudes of the raw image received by the artifact coil and the raw image received by the non-artifact coil to obtain the composite image.

11. The magnetic resonance imaging system according to claim 9, wherein the composition module is used for extracting a root from a sum of a conjugate product of the raw image received by the artifact coil and space sensitivity of its coil and a conjugate product of the raw image received by the non-artifact coil and space sensitivity of its coil to obtain the composite image.

12. The magnetic resonance imaging system according to claim 9, further comprising a coil determining module for determining a receiving coil whose distance from an artifact source is within a preset range as an artifact coil and determining a receiving coil whose distance from the artifact source is outside the preset range as a non-artifact coil.

13. The magnetic resonance imaging system according to claim 12, further comprising a first artifact source determining module for analyzing a magnetic resonance image to determine a 3D position coordinate on which an artifact is generated in the magnetic resonance imaging system and determining a position of the artifact source according to said 3D position coordinate.

14. The magnetic resonance imaging system according to claim 12, further comprising a second artifact source determining module for emulating a gradient coil in the magnetic resonance imaging system, determining a 3D position coordinate on which an artifact is generated according to an emulating result, and determining a position of the artifact source according to said 3D position coordinate.

15. The magnetic resonance imaging system according to claim 9, wherein the correction module is used for multiplying a module of the composite image by the space sensitivity of the artifact coil and phase distribution information of the raw image received by said artifact coil to replace the raw image received by the artifact coil.

16. The magnetic resonance imaging system according to claim 9, further comprising a second judgment module for judging whether the number of times for obtaining a composite image by the composition module has reached a preset value; if it has, controlling the correction module and the composition module to stop operating; if it has not, controlling the correction module and the composition module to operate again.

* * * * *